US012233069B2

(12) United States Patent
Qiu et al.

(10) Patent No.: US 12,233,069 B2
(45) Date of Patent: Feb. 25, 2025

(54) ORAL SOLID TABLET COMPRISING BRUTON'S TYROSINE KINASE INHIBITOR AND PREPARATION METHOD THEREFOR

(71) Applicant: BEIGENE SWITZERLAND GMBH, Basel (CH)

(72) Inventors: Gang Qiu, Beijing (CN); Yiwei Shen, Beijing (CN); Wenyuan Fan, Beijing (CN); Shuo Xu, Beijing (CN); Huiru Lv, Beijing (CN); Jialin Bian, Beijing (CN); Zhengming Du, Beijing (CN)

(73) Assignee: BeiGene Switzerland GmbH, Basel (CH)

( * ) Notice: Subject to any disclaimer, the term of this patent is extended or adjusted under 35 U.S.C. 154(b) by 0 days.

(21) Appl. No.: 18/388,898

(22) Filed: Nov. 13, 2023

(65) Prior Publication Data

US 2024/0075039 A1  Mar. 7, 2024

Related U.S. Application Data

(63) Continuation of application No. 17/617,530, filed as application No. PCT/CN2020/095352 on Jun. 10, 2020, now abandoned.

(30) Foreign Application Priority Data

Jun. 10, 2019 (WO) ................ PCT/CN2019/090541

(51) Int. Cl.
*A61K 31/519* (2006.01)
*A61K 9/20* (2006.01)
*A61K 9/28* (2006.01)

(52) U.S. Cl.
CPC .......... *A61K 31/519* (2013.01); *A61K 9/2009* (2013.01); *A61K 9/2013* (2013.01);
(Continued)

(58) Field of Classification Search
None
See application file for complete search history.

(56) References Cited

U.S. PATENT DOCUMENTS 7,393,848 B2  7/2008 Currie
7,514,444 B2  4/2009 Honigberg
(Continued)

FOREIGN PATENT DOCUMENTS

CN  1771231 A   5/2006
CN  102656173 A  9/2012
(Continued)

OTHER PUBLICATIONS

Varma. Excipients used in the formulation of tablets. Research and reviews: Journal of Chemistry, vol. 5:2, p. 143-154 (Year: 2016).*
(Continued)

*Primary Examiner* — Lakshmi S Channavajjala
(74) *Attorney, Agent, or Firm* — Ice Miller LLP

(57) ABSTRACT

Provided are an oral solid tablet comprising (S)-7-[4-(1-acryloylpiperidine)]-2-(4-phenoxyphenyl)-4,5,6,7-tetrahydropyrazolo[1,5-a]pyrimidine-3-carboxamide and preparation method therefor. The oral solid tablet has good drug release characteristics, features easy administration, quick and high-efficient release, no particular requirements on equipment, and a simple formulation preparation process, can ensure formulation stability and facilitate transportation and storage, and is suitable for large-scale production.

23 Claims, 2 Drawing Sheets

(52) U.S. Cl.
CPC .......... *A61K 9/2018* (2013.01); *A61K 9/2054* (2013.01); *A61K 9/2866* (2013.01)

(56) References Cited

U.S. PATENT DOCUMENTS

| | | |
|---|---|---|
| 7,718,662 B1 | 5/2010 | Chen |
| 8,084,620 B2 | 12/2011 | Liu |
| 8,735,553 B1 | 5/2014 | Li |
| 9,447,106 B2 | 9/2016 | Wang |
| 9,556,188 B2 | 1/2017 | Wang |
| 10,005,782 B2 | 6/2018 | Wang |
| 10,570,139 B2 | 2/2020 | Wang |
| 10,927,117 B2 | 2/2021 | Wang |
| 11,142,528 B2 | 10/2021 | Wang |
| 2002/0094989 A1 | 7/2002 | Hale |
| 2006/0178367 A1 | 8/2006 | Currie |
| 2006/0183746 A1 | 8/2006 | Currie |
| 2008/0076921 A1 | 3/2008 | Honigberg |
| 2008/0139582 A1 | 6/2008 | Honigberg |
| 2009/0105209 A1 | 4/2009 | Dewdney |
| 2009/0318441 A1 | 12/2009 | Brain |
| 2010/0004231 A1 | 1/2010 | Dewdney |
| 2010/0016296 A1 | 1/2010 | Singh |
| 2010/0016301 A1 | 1/2010 | Dewdney |
| 2010/0029610 A1 | 2/2010 | Singh |
| 2010/0035841 A1 | 2/2010 | Jankowski |
| 2010/0087464 A1 | 4/2010 | Mi |
| 2010/0105676 A1 | 4/2010 | Liu |
| 2010/0144705 A1 | 6/2010 | Miller |
| 2010/0160292 A1 | 6/2010 | Whitney |
| 2010/0160303 A1 | 6/2010 | Liu |
| 2010/0222325 A1 | 9/2010 | Berthel |
| 2010/0249092 A1 | 9/2010 | Singh |
| 2010/0254905 A1 | 10/2010 | Honigberg |
| 2011/0118233 A1 | 5/2011 | Blomgren |
| 2011/0124640 A1 | 5/2011 | Liu |
| 2011/0224235 A1 | 9/2011 | Honigberg |
| 2011/0301145 A1 | 12/2011 | Barbosa Jr. |
| 2011/0318321 A1 | 12/2011 | Selva |
| 2012/0028981 A1 | 2/2012 | Miller |
| 2012/0040961 A1 | 2/2012 | Gray |
| 2012/0053189 A1 | 3/2012 | Loury |
| 2012/0058996 A1 | 3/2012 | Liu |
| 2012/0077832 A1 | 3/2012 | Witowski |
| 2012/0082702 A1 | 4/2012 | Delucca |
| 2012/0129852 A1 | 5/2012 | Duan |
| 2012/0157442 A1 | 6/2012 | Bui |
| 2012/0157443 A1 | 6/2012 | Bui |
| 2012/0232054 A1 | 9/2012 | Moriarty |
| 2013/0079327 A1 | 3/2013 | Yamamoto |
| 2013/0096118 A1 | 4/2013 | Liu |
| 2013/0116213 A1 | 5/2013 | Cha |
| 2013/0261103 A1 | 10/2013 | Currie |
| 2013/0281432 A1 | 10/2013 | Currie |
| 2014/0045833 A1 | 2/2014 | Laurent |
| 2014/0094459 A1 | 4/2014 | Goldstein |
| 2014/0107151 A1 | 4/2014 | Goldstein |
| 2014/0162983 A1 | 6/2014 | Hodous |
| 2014/0221398 A1 | 8/2014 | Goldstein |
| 2014/0243306 A1 | 8/2014 | Heng |
| 2015/0079109 A1 | 3/2015 | Li |
| 2015/0259354 A1 | 9/2015 | Wang |
| 2015/0315274 A1 | 11/2015 | Li |
| 2016/0083392 A1 | 3/2016 | Wang |
| 2017/0073349 A1 | 3/2017 | Wang |
| 2018/0251466 A1 | 9/2018 | Wang |
| 2018/0360853 A1 | 12/2018 | He |
| 2019/0169201 A1 | 6/2019 | Wang |
| 2020/0148690 A1 | 5/2020 | Wang |
| 2020/0181150 A1 | 6/2020 | Wang |
| 2020/0368237 A1 | 11/2020 | Hilger |
| 2021/0130363 A1 | 5/2021 | Wang |
| 2021/0275530 A1 | 9/2021 | Hu |
| 2021/0330643 A1* | 10/2021 | Brandhuber ......... A61K 9/1652 |
| 2021/0332049 A1 | 10/2021 | Guo |

FOREIGN PATENT DOCUMENTS

| | | | |
|---|---|---|---|
| CN | 104884458 A | 9/2015 | |
| CN | 107530348 A | 1/2018 | |
| CN | 108778281 | 11/2018 | |
| CN | 113939289 A | 1/2022 | |
| GB | 1412017 A | 10/1975 | |
| JP | H07278148 A | 10/1995 | |
| JP | 2006510582 A | 3/2006 | |
| JP | 2012515738 | 7/2012 | |
| JP | 2017081859 | 5/2017 | |
| WO | 0119829 A2 | 3/2001 | |
| WO | 2001016138 A1 | 3/2001 | |
| WO | 2002050071 A1 | 6/2002 | |
| WO | 2002072576 A1 | 9/2002 | |
| WO | 2003004497 A1 | 1/2003 | |
| WO | 2004017908 A2 | 3/2004 | |
| WO | 2005005429 A1 | 1/2005 | |
| WO | 2005011597 A2 | 2/2005 | |
| WO | 2005014599 A1 | 2/2005 | |
| WO | 2005047290 A2 | 5/2005 | |
| WO | 2006053121 A2 | 5/2006 | |
| WO | 2006065946 A1 | 6/2006 | |
| WO | 2006099075 A2 | 9/2006 | |
| WO | 2007026720 A1 | 3/2007 | |
| WO | 2007026950 A1 | 3/2007 | |
| WO | 2007027594 A1 | 3/2007 | |
| WO | 2007027729 A1 | 3/2007 | |
| WO | 2007087068 A2 | 8/2007 | |
| WO | 2007136790 A2 | 11/2007 | |
| WO | 2008033834 A1 | 3/2008 | |
| WO | 2008033854 A1 | 3/2008 | |
| WO | 2008033857 A2 | 3/2008 | |
| WO | 2008039218 A2 | 4/2008 | |
| WO | 2008054827 A2 | 5/2008 | |
| WO | 2008144253 A1 | 11/2008 | |
| WO | 2009039397 A2 | 3/2009 | |
| WO | 2009051822 A1 | 4/2009 | |
| WO | 2009077334 A1 | 6/2009 | |
| WO | 2009098144 A1 | 8/2009 | |
| WO | 2009158571 A1 | 12/2009 | |
| WO | 2010000633 A1 | 1/2010 | |
| WO | 2010006947 A1 | 1/2010 | |
| WO | 2010006970 A1 | 1/2010 | |
| WO | 2010028236 A1 | 3/2010 | |
| WO | 2010051549 A1 | 5/2010 | |
| WO | 2010065898 A2 | 6/2010 | |
| WO | 2010068788 A1 | 6/2010 | |
| WO | 2010068806 A1 | 6/2010 | |
| WO | 2010068810 A2 | 6/2010 | |
| WO | 2010092925 | 8/2010 | |
| WO | 2010122038 A1 | 10/2010 | |
| WO | 2011006074 A1 | 1/2011 | |
| WO | 2011140488 A1 | 11/2011 | |
| WO | 2011153514 A2 | 12/2011 | |
| WO | 2012020008 A1 | 2/2012 | |
| WO | 2012135801 A1 | 10/2012 | |
| WO | 2012143522 A1 | 10/2012 | |
| WO | 2012156334 A1 | 11/2012 | |
| WO | 2012158795 A1 | 11/2012 | |
| WO | WO-2014173289 A1 * | 10/2014 | ......... A61K 31/4188 |
| WO | 2015035606 A1 | 3/2015 | |
| WO | 2015061752 A1 | 4/2015 | |
| WO | 2016008411 A1 | 1/2016 | |
| WO | 2016024228 A1 | 2/2016 | |
| WO | 2016025720 A1 | 2/2016 | |
| WO | 2016087994 A1 | 6/2016 | |
| WO | 2016100914 A1 | 6/2016 | |
| WO | 2016105582 A1 | 6/2016 | |
| WO | 2016123504 | 8/2016 | |
| WO | 2017046746 A1 | 3/2017 | |
| WO | 2017059224 A2 | 4/2017 | |
| WO | 2018033853 A2 | 2/2018 | |
| WO | WO-2018033135 A1 * | 2/2018 | ........... A61K 31/519 |
| WO | 2018137681 A1 | 8/2018 | |
| WO | 2018193105 A1 | 10/2018 | |
| WO | 2019034009 A1 | 2/2019 | |
| WO | 2019108795 A1 | 6/2019 | |

(56) References Cited

FOREIGN PATENT DOCUMENTS

| WO | 2019183226 A1 | 9/2019 |
|---|---|---|
| WO | 2020249001 A1 | 12/2020 |
| WO | 2020249002 A1 | 12/2020 |

OTHER PUBLICATIONS

Chu et al. Effect of particle size on the dissolution behaviors of poorly water soluble drugs. Arch. Pharm. Res. vol.35, No. 7, p. 1187-1195. (Year: 2012).*

Balbach, S., et al., "Pharmaceutical evaluation of early development candidates: 'The 100 mg-approach'," International Journal of Pharmaceutics, 2004, vol. 275 pp. 1-12.

Beigene Co., Ltd., "Phase I Clinical Research to Evaluate Safety, Tolerability and Pharmacokinetics/ Pharmacodynamics Characteristics of BTK Inhibitor, BGB-3111, in Treating Chinese B Lymphocyte Tumor Patients," [Online], May 2016, Retrieved from the Internet: http://www.chinadrugtrials.org.cn/clinicaltrials.searchlistdetail.dhtml, Retrieved on: Mar. 21, 2022, 17 pages (with Machine Translation).

Beigene, "Efficacy and Safety of Zanubrutinib in Relapsed or Refractory Chronic Lymphocytic Leukemia/Small Lymphocytic Lymphoma," [Online], Jul. 2017, Retrieved from the Internet: https://clinicaltrials.gov/ct2/show/NCT03206918, Retrieved on: Apr. 4, 2022, 7 pages.

Bradshaw, J. M., "The Src, Syk, and Tec family kinases: distinct types of molecular switches," Cell Signal., Aug. 2010, 22(8)1175-1184.

Caira, M. R., "Crystalline Polymorphism of Organic Compounds," Topics in Current Chemistry, Jan. 1, 1998, vol. 198, pp. 163-208.

Cartigny, D. et al., "General Asymmetric Hydrogenation of 2-Alkyl- and 2-Aryl-Substituted Quinoxaline Derivatives Catalyzed by Iridium-Difluorphos: Unusual Halide Effect and Synthetic Application," J. Org. Chem., Apr. 2012, vol. 77, No. 10, pp. 4544-4556.

Conley, M. E. et al., "Primary B Cell Immunodeficiencies: Comparisons and Contrasts," Annu. Rev. Immunol., Apr. 23, 2009, vol. 27, pp. 199-227.

Davis, R. E. et al., "Chronic active B-cell-receptor signaling in diffuse large B-cell lymphoma," Nature 463:88-92 (2019).

Extended European Search Report for European Application No. 14787642.9, mailed Jan. 26, 2016, 5 pages.

Extended European Search Report for European Application No. 17841107.0, mailed Feb. 21, 2020, 12 pages.

Extended European Search Report for European Application No. 17841172.4, mailed Mar. 5, 2020, 6 pages.

Extended European Search Report for European Application No. 18744173.8, mailed Oct. 21, 2020, 12 pages.

Guan Xianyu et al., Pharmaceutical Excipients and Packaging Materials, p. 87, 2016.

Gurcan, H.M. et al., "A review of the current use of rituximab in autoimmune diseases," Int. Immunopharmacol., Jan. 2009, vol. 9, No. 1, pp. 10-25.

Hackam et al., "Translation of research evidence from animals to humans," JAMA, Oct. 11, 2006, vol. 296, No. 14, pp. 1727-1732.

Humphries, L. A. et al., "Tec kinases mediate sustained calcium influx via site-specific tyrosine phosphorylation of the phospholipase Cgamma Src homology 2-Src homology 3 linker," J. Biol.Chem., Sep. 2004, vol. 279, No. 36, pp. 37651-37661.

International Search Report and Written Opinion for International Application No. PCT/CN2014/075943, mailed Jul. 18, 2014, 10 pages.

International Search Report and Written Opinion for International Application No. PCT/CN2017/098023, mailed Nov. 16, 2017, 10 pages.

International Search Report and Written Opinion for International Application No. PCT/CN2018/074108, mailed Apr. 23, 2018, 12 pages.

International Search Report and Written Opinion for International Application No. PCT/CN2018/100145, mailed Nov. 14, 2018, 8 pages.

International Search Report and Written Opinion for International Application No. PCT/CN2020/095352, mailed Sep. 16, 2020, 23 pages.

International Search Report and Written Opinion for International Application No. PCT/CN2020/095353, mailed Sep. 15, 2020, 23 pages.

International Search Report and Written Opinion for International Application No. PCT/IB2017/054955, mailed Sep. 10, 2018, 16 pages.

International Search Report and Written Opinion for International Application No. PCT/US2018/063068, mailed Feb. 27, 2019, 8 pages.

Jenkins, S. M. et al., "Substituent variation in azabicyclictriazole- and tetrazole-based muscarinic receptor ligands," J. Med. Chem., 35(13):2392-2406 (1992).

Jie, L., "Deuterated Drugs Progress," Chemical Engineering Design Communication Medicine and Chemical Industry, 2016, vol. 42, No. 4, p. 199.

Jordan "Tamoxifen: a most unlikely pioneering medicine," Nature Reviews Drug Discovery, Mar. 2003, vol. 2, No. 3, pp. 205-213.

Kersseboom, R. et al., "Constitutive activation of Bruton's tyrosine kinase induces the formation of autoreactive IgM plasma cells," Eur. J. Immunol., Sep. 2010, vol. 40, pp. 2643-2654.

Khan, W. N., "Regulation of B lymphocyte development and activation by Bruton's tyrosine kinase," Immunol. Res., Apr. 2001, vol. 23, pp. 147-156.

Kim, K.-H. et al., "Imidazo[1,5-a]quinoxalines as irreversible BTK inhibitors for the treatment of rheumatoid arthritis," Bioorg. Med. Chem. Lett., Nov. 1, 2011, vol. 21, No. 21, pp. 6258-6263.

Li, N. et al., "BGB-3111 is a novel and highly selective Bruton's tyrosine kinase (BTK) inhibitor," Cancer Center, vol. 75, No. 15, Supp. 1, Abstract No. 2597, 106th Annual Meeting of the American Association for Cancer Research, AACR 2015, Philadelphia, PA, United States, Aug. 2015, 2 pages.

Lou, Y. et al., "Bruton's tyrosine kinase inhibitors: Approaches to potent and selective inhibition, preclinical and clinical evaluation for inflammatory diseases and B cell malignancies," J. Med. Chem., 55(10):4539-4550 (2012).

Luo, J. et al., "Modern Physical Pharmaceutics Theory and Practice," Shang Hai Science and Technology Literature Publishing House, Apr. 2005, pp. 293-295.

MedChemExpress, "Zanubrutinib," Product Data Sheet, Retrieved from the Internet: www.medchemexpress.com, Retrieved Aug. 17, 2021,2 pages.

Mohamed, A. J. et al., "Bruton's tyrosine kinase (Btk): function, regulation, and transformation with special emphasis on the PH domain," Immunol. Rev., 228:58-73 (2009).

Office Action for Japanese Application No. 2019-508889, mailed Jun. 22, 2021, 7 pages.

Pan, Z, "Bruton's tyrosine kinase as a drug discovery target," Drug News Perspect, Sep. 1, 2008, vol. 21, No. 7, pp. 357-362.

Pan, Z. et al., "Discovery of Selective Irreversible Inhibitors for Bruton's Tyrosine Kinase," ChemMedChem, Jan. 2007, vol. 2, No. 1, pp. 58-61.

Rokosz, L. L. et al., "Kinase inhibitors as drugs for chronic inflammatory and immunological diseases: progress and challenges," Expert Opin. Ther. Targets, 12(7):883-903 (2008).

Singhal, D., et al., "Drug Polymorphism and Dosage Form Design: A practical perspective", Advanced Drug Delivery Reviews (2004); 56: 335-347.

Smith, C. I. et al., "Expression of Bruton's agammaglobulinemia tyrosine kinase gene, BTK, is selectively down- regulated in T lymphocytes and plasma cells," J. Immunol., Jan. 1994, vol. 152, No. 2, pp. 557-565.

Takada, N., "Bulk Drug Form Screening and Selection at Drug Discovery Phase," Pharm Stage, Jan. 2007, vol. 6, No. 10, pp. 20-25.

Takayama, T. et al., "Effects of the novel and potent lymphocyte-specific protein tyrosine kinase inhibitor TKM0150 on mixed

(56) References Cited

OTHER PUBLICATIONS lymphocyte reaction and contact hypersensitivity in mice," Arzneimittelforschung, 60(5):282-285 (2010).
Takayama, T. et al., "Ring-fused pyrazole derivatives as potent inhibitors of lymphocyte-specific kinase (Lck): Structure, synthesis, and SAR," Bioorganic & Medicinal Chemistry Letters, Jan. 2010, vol. 20, No. 1, pp. 112-116.
Tam, C. S. et al., "A head-to-head Phase III study comparing zanubrutinib versus ibrutinib in patients with Waldenstrom macroglobulinemia," Future Oncology, Sep. 2018, vol. 14, No. 22, pp. 2229-2237.
Uckun, F. M. et al., "Bruton's tyrosine kinase as a new therapeutic target," Anti-Cancer Agents in Medicinal Chemistry, Nov. 1, 2007, vol. 7, No. 6, pp. 624-632.
Vetrie, D. et al., "The gene involved in X-linked agammaglobulinaemia is a member of the src family of protein-tyrosine kinases," Nature, Jan. 21, 1993, vol. 361, No. 6409, pp. 226-233.
Wilson, W. H. et al., "686—The Bruton's Tyrosine Kinase (Btk) Inhibitor, Ibrutinib (PCI-32765), Has Preferential Activity in the ABC Subtype of Relapsed/Refractory De Novo Diffuse Large B-Cell Lymphoma (DLBCL): Interim Results of a Multicenter, Open-Label, Phase2 Study," Poster #686, 54th American Society of Hematology (ASH) Annual Meeting Abstract (Dec. 10, 2012), 3 pages.
Hirayama, Y., "Handbook for organic compound crystal—Principle and Know-how," 2008, 28 pages.
Shioji, Y., "Production Technology of Solid Preparations," Tokyo, CMC Publication, Jan. 27, 2003, Popular Edition, pp. 9 and 12-13.
Humphries et al., "Tee Kinases Mediate Sustained Calcium Influx via Site—specific Tyrosine Phosphorylation of the Phospholipase C Src Homology 2-Src Homology 3 Linker", J. Biol. Chem., 279(36): 37651-37661, 2004.

\* cited by examiner

ORAL SOLID TABLET COMPRISING BRUTON'S TYROSINE KINASE INHIBITOR AND PREPARATION METHOD THEREFOR

CROSS-REFERENCE TO RELATED APPLICATIONS

This application is a continuation of U.S. application Ser. No. 17/617,530, filed on Dec. 8, 2021, which is a U.S. National Stage Application under 35 U.S.C. § 371 of International Application No. PCT/CN2020/095352, filed Jun. 10, 2020, which claims priority to Patent Application No. PCT/CN2019/090541 (CN), filed on Jun. 10, 2019.

TECHNICAL FIELD

The present invention relates to an solid tablet for oral administration containing a Bruton's Tyrosine Kinase (BTK) inhibitor, in particular (S)-7-[4-(1-acryloylpiperidine)]-2-(4-phenoxyphenyl)-4,5,6,7-tetrahydropyrazolo[1,5-a]pyrimidine-3-carboxamide and a preparation method thereof.

BACKGROUND ART

International application WO 2014173289 A disclosed a novel Bruton's Tyrosine Kinase (BTK), more particularly (S)-7-[4-(1-acryloylpiperidine)]-2-(4-phenoxyphenyl)-4,5,6,7-tetrahydropyrazolo[1,5-a] pyrimidine-3-carboxamide (with a generic name of Zanubrutinib), which has a chemical structure as follows:

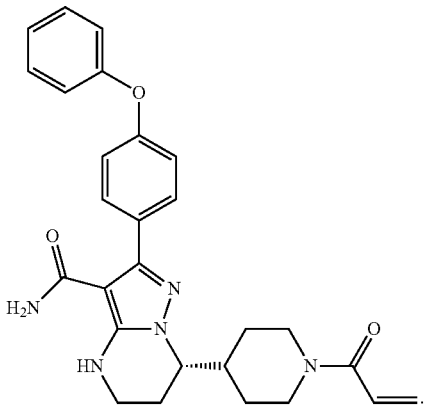 [SMILES: C=CC(=O)N1CCC([C@@H]2CCNc3c(C(N)=O)c(-c4ccc(Oc5ccccc5)cc4)nn32)CC1]

Zanubrutinib belongs to the second-generation BTK inhibitor, which irreversibly inactivates the tyrosine kinase by covalently binding with the enzyme. It is used as a single agent or in combination with other drugs for the treatment of B lymphocyte tumors, including chronic lymphocytic leukemia/small lymphocytic lymphoma (CLL/SLL), mantle cell lymphoma (MCL), Waldenstrom's macroglobulinemia (WM), follicular lymphoma (FL), non-germinal center subtype diffuse large B-cell lymphoma (non-GCB DLBCL), etc.

The active pharmaceutical ingredient of Zanubrutinib is slightly hygroscopic. DSC results show that the compound has a distinct endothermic peak when it melts, and has an initial temperature and a peak temperature of 139° C. and 144° C., respectively. The melting point of the active pharmaceutical ingredient is 145° C., which is lower than the ideal melting point of 150° C. for tablet development, and the material is relatively viscous, which poses a huge challenge to the development and large-scale industrial production of Zanubrutinib tablets. In addition, the Zanubrutinib has a pH-dependent solubility and belongs to class II (low solubility, and high permeability) drug of the biopharmaceutical classification system. Therefore, there is an urgent need to develop a Zanubrutinib tablet in which the active ingredient can dissolve quickly from the preparation, so as to maintain the rapid release of the drug in the whole intestine with good bioavailability.

SUMMARY OF THE INVENTION

In order to overcome the deficiencies in the physicochemical properties of Zanubrutinib active pharmaceutical ingredient (API), such as high viscosity, poor fluidity, and poor solubility, etc., and to ensure good dissolution of the drug, the present invention provides an solid tablet for oral administration containing Bruton's Tyrosine Kinase inhibitor of Zanubrutinib and a preparation method thereof. The inventors of the present invention unexpectedly discovered that a certain amount of colloidal silica as a glidant and other excipients have a significant contribution to improve the sticking of the drug and ensure a good dissolution rate of the drug. The solid tablet for oral administration of Zanubrutinib of the present invention can be released relatively quickly in a medium containing sodium lauryl sulfate at pH 1.2 (HCl), for example, the dissolution rate can reach more than 80% within 30 to 60 min at some prescription excipient ratios; preferably, the dissolution rate of Zanubrutinib can reach more than 95% within 30 min at some prescription excipient ratios. In addition, the solid tablet for oral administration of Zanubrutinib of the present invention has no special requirements for production equipment, has a simple preparation process, a stable product, and low production costs.

In one aspect of the present invention, there is provided an solid tablet for oral administration containing Zanubrutinib, comprising: (1) 20% to 70% (mass percentage), preferably 30% to 50% (mass percentage) of Zanubrutinib; and (2) one or more pharmaceutically acceptable excipients.

In some embodiments of the present invention, the Zanubrutinib may be in any solid form thereof, such as a crystal form (e.g., crystal form A disclosed in WO 2018033853 A), an amorphous form, or a mixture of a crystal form and an amorphous form. Preferably, the solid tablet for oral administration is of a crystal form A, an amorphous form, or a mixture of a crystal form A and an amorphous form. In some specific embodiments of the present invention, the particle size of the Zanubrutinib is no more than 40 μm.

In some embodiments, the X-ray powder diffraction pattern of crystal form A includes diffraction peaks having 2θ angle values independently selected from: about 14.8±0.2°, 15.6±0.2°, 16.4±0.2° and 21.4±0.2°. In some embodiments, the X-ray powder diffraction pattern of crystal form A includes diffraction peaks having 2θ angle values independently selected from: about 12.2±0.2°, 12.9±0.2°, 14.8±0.2°, 15.6±0.2°, 16.4±0.2° and 21.4±0.2°. In some embodiments, the X-ray powder diffraction pattern of crystal form A includes diffraction peaks having 2θ angle values independently selected from: about 12.2±0.2°, 12.9±0.2°, 14.8±0.2°, 15.6±0.2°, 16.4±0.2°, 17.7±0.2°, 18.5±0.2°, 20.7±0.2° and 21.4±0.2°. In some embodiments, the X-ray powder diffraction pattern of crystal form A is substantially consistent with FIG. 1.

In some embodiments of the present invention, the excipient is optionally selected from a filler, a binder, a disintegrant, a wetting agent, a glidant, a lubricant, and any combination thereof.

In some specific embodiments of the present invention, the filler is selected from starch, sucrose, microcrystalline cellulose, mannitol, lactose, pregelatinized starch, glucose, maltodextrin, cyclodextrin, cellulose, silicified microcrystalline cellulose, and any combination thereof.

In some specific embodiments of the present invention, the filler is lactose in a content of about 20% to 70%, preferably about 40% to 60%, all in mass percentages.

In some specific embodiments of the present invention, the filler is microcrystalline cellulose, the microcrystalline cellulose is internal filler, and the content of the microcrystalline cellulose filler is about 10% to 50%, preferably about 30% to 50%, all in mass percentages.

In some specific embodiments of the present invention, the filler is a combination of lactose and microcrystalline cellulose, and the contents of the lactose and the microcrystalline cellulose are about 0% to 70% and about 0% to 50%, preferably about 40% to 60% and about 4% to 10%, respectively, all in mass percentages.

In some embodiments of the present invention, the binder is selected from starch, hypromellose, polyvinylpyrrolidone, sodium carboxymethyl cellulose, hydroxypropyl cellulose, methyl cellulose, ethyl cellulose, gelatin, sucrose, and any combination thereof.

In some specific embodiments of the present invention, the binder is hypromellose, and the content of the hypromellose is about 0% to 10%, preferably about 0% to 5%, all in mass percentages.

In some specific embodiments of the present invention, the binder is croscarmellose sodium in a content of about 0% to 10%, preferably about 0% to 5%, all in mass percentages.

In some embodiments of the present invention, the disintegrant is selected from sodium carboxymethyl starch, low-substituted hydroxypropyl cellulose, crospovidone, croscarmellose sodium, croscarmellose, methyl cellulose, pregelatinized starch, sodium alginate, and any combination thereof.

In some specific embodiments of the present invention, the disintegrant is croscarmellose sodium, and the content of the croscarmellose sodium is about 0.5% to 5%, preferably about 1% to 3%, all in mass percentages.

In some embodiments of the present invention, the wetting agent is sodium lauryl sulfate (SLS), and the content of the sodium lauryl sulfate is about 0% to 5%, preferably about 0.5% to 1.0%, all in mass percentages.

In some embodiments of the present invention, the glidant is selected from powdered cellulose, magnesium trisilicate, colloidal silica, talc powder, and any combination thereof.

In some specific embodiments of the present invention, the glidant is colloidal silica, and the content of the colloidal silica is about 0.1% to 20%, which is mass percentage. When the content of the colloidal silica is less than 0.1% (mass percentage), colloidal silica cannot effectively disperse the API, as a result, the rapid disintegration of the tablets and the dissolution of the API cannot be guaranteed; When the content of the colloidal silica is greater than 20% (mass percentage), it is unfavourable for commercialized production due to its huge volume. More preferably, the content of the colloidal silica is about 4% to 8%, in mass percentage.

In some embodiments of the present invention, the lubricant is selected from zinc stearate, glyceryl monostearate, glyceryl palmitate stearate, magnesium stearate, sodium fumarate stearate, and any combination thereof.

In some specific embodiments of the present invention, the lubricant is magnesium stearate in a content of about 0.1% to 2%, preferably about 0.3% to 1%, all in mass percentages.

Still further, the Zanubrutinib solid tablet for oral administration provided by the present invention further comprises a coating agent.

In some embodiments of the present invention, the coating agent is selected from an Opadry film coating powder, polyvinyl alcohol, hydroxypropyl cellulose, polyethylene glycol, and any combination thereof. The Opadry film coating powder is preferred.

In one aspect of the present invention, the present invention provides a method for preparing the Zanubrutinib oral solid preparation, and the granulation process of which is selected from direct powder compression, dry granulation, and wet granulation, preferably wet granulation.

In one aspect of the present invention, the present invention provides a method for preparing the Zanubrutinib solid tablet for oral administration, which comprises the following steps:
(1) mixing a Zanubrutinib active pharmaceutical ingredient and excipients (including but not limited to, a filler, a binder, a disintegrant, a wetting agent, a glidant, and a lubricant);
(2) subjecting the mixture of the zanubrutinib active pharmaceutical ingredient and excipients to wet granulation with purified water, or an organic reagent (including but not limited to ethanol, acetone), or an aqueous solution or an organic solution containing a binder, followed by drying and sizing;
(3) optionally, mixing the sized granules with an additional excipient (including but not limited to a filler, a lubricant, a glidant) and compressing them into plain tablets;
(4) optionally, coating the plain tablets,
wherein if step (3) is not performed, the sized granules obtained in step (2) are compressed into plain tablets.

In some embodiments of the present invention, the organic reagent in step (2) is selected from ethanol, acetone, and a combination thereof.

In some embodiments of the present invention, the additional excipient described in step (3) is selected from a filler (e.g., microcrystalline cellulose), a lubricant (e.g., magnesium stearate), a glidant (e.g., colloidal silica), and any combination thereof.

In the above-mentioned preparation method, the specific examples and contents of a filler, a binder, a disintegrant, a wetting agent, a glidant, a lubricant and a coating are as described above.

In the above-mentioned preparation method, the "mixing" in the above-mentioned preparation step (1) is carried out by a commonly used mixing method. An apparatus, for example, a hopper mixer, a vertical granulator, FLO-5M, V-type mixer, a tumbler mixer, etc., is used for "mixing".

In the above-mentioned preparation method, the granulation in the above-mentioned preparation step (2) can be carried out by a common granulation method. The granulation is carried out by an apparatus, such as a wet granulator, etc. The compression is carried out by a conventional tablet press, such as ZP10A. After the tablet is made, it can be "dried", if necessary. For drying, any method used to dry the preparation can generally be used, for example, vacuum drying, fluidized bed drying, etc. The following terms that can be used herein are used according to the following definitions.

Unless it is clearly indicated to the contrary, all ranges referred herein are inclusive; that is, the range includes the values of the upper and lower limits of the range and all values therebetween. For example, the temperature range, percentage, equivalent range, etc., described herein include the upper and lower limits of the range and any value in the continuous interval therebetween.

As used herein, the term "mass percentage" describes the contents of the Zanubrutinib active pharmaceutical ingredient and various excipients, which is calculated with respect to the total mass of the solid tablet for oral administration.

The term "preparation" as used herein refers to a mixture, an aggregate, a solution or other combinations of substances including the active pharmaceutical ingredients (APIs); the preparation is suitable for a particular route of administration, for example, is suitable for compression into a preparation of a tablet that is designed for oral administration in the treatment, management, and prevention, etc., of the patient's disease states or disorders.

The "coating" as used herein is not limited to the case of coating the entire surface of the coated object (a plain tablet containing Zanubrutinib), but can also refers to the partial coating of the coated object, absorbing or adsorbing the enteric-coating components onto the coated object, or plain tablets with an inner core coated. The solid tablet for oral administrations prepared according to the present invention have a hardness of 60 N to 220 N, and the dissolution rate exceeds 85% within 30 minutes.

In some embodiments of the present invention, the content of Zanubrutinib in the solid oral tablet is usually about 70 mg to about 400 mg of Zanubrutinib per tablet, preferably about 80 mg, 160 mg or 320 mg of Zanubrutinib.

In some embodiments of the present invention, the solid oral tablet may also contain one or more agents selected from a sweetening agent, a corrective, a colouring agent and a preservative to provide a pharmaceutically aesthetic and palatable preparation.

In some embodiments of the present invention, the solid oral tablet can be prepared in a variety of possible shapes (ellipsoid, capsule, double-sided convex round lamp).

DETAILED DESCRIPTION OF EMBODIMENTS

The following examples can help those skilled in the art to understand the present invention more comprehensively, but do not limit the present invention in any way. In the following, unless otherwise specified, the temperature is in ° C. Reagents are purchased from commercial providers such as Sigma-Aldrich, Alfa Aesar or TCI, and can be used without further purification unless otherwise specified.

Example 1

Preparation of Solid Tablet for Oral Administrations of Zanubrutinib, Specification: 160 mg
Prescription (Per 100 g Plain Tablets):

| | |
|---|---|
| Zanubrutinib (Crystal form A) | 34.8 g |
| Lactose | 53.2 g |
| Croscarmellose sodium | 2 g |
| Colloidal silica | 4.5 g |
| Sodium lauryl sulfate | 1 g |
| Microcrystalline cellulose | 4 g |
| Magnesium stearate | 0.5 g |
| Opadry | 2.4 g |

Preparation Process: 53.2 g of lactose, 2 g of croscarmellose sodium, 1 g of sodium lauryl sulfate and 34.8 g of Zanubrutinib are added into a high-shear granulator (MYCROMIX, manufactured by BOSCH) and mixed for 5 minutes, an appropriate amount of purified water is added for granulation, followed by dying and then sizing, 4.5 g of colloidal silica, 4 g of microcrystalline cellulose and 0.5 g of magnesium stearate are further added and mixed. After mixing, the above ingredients are pressed into tablets to obtain plain tablets. The above-mentioned plain tablets are coated with 2.4 g of Opadry to obtain solid tablet for oral administrations containing Zanubrutinib.

Figure 1:
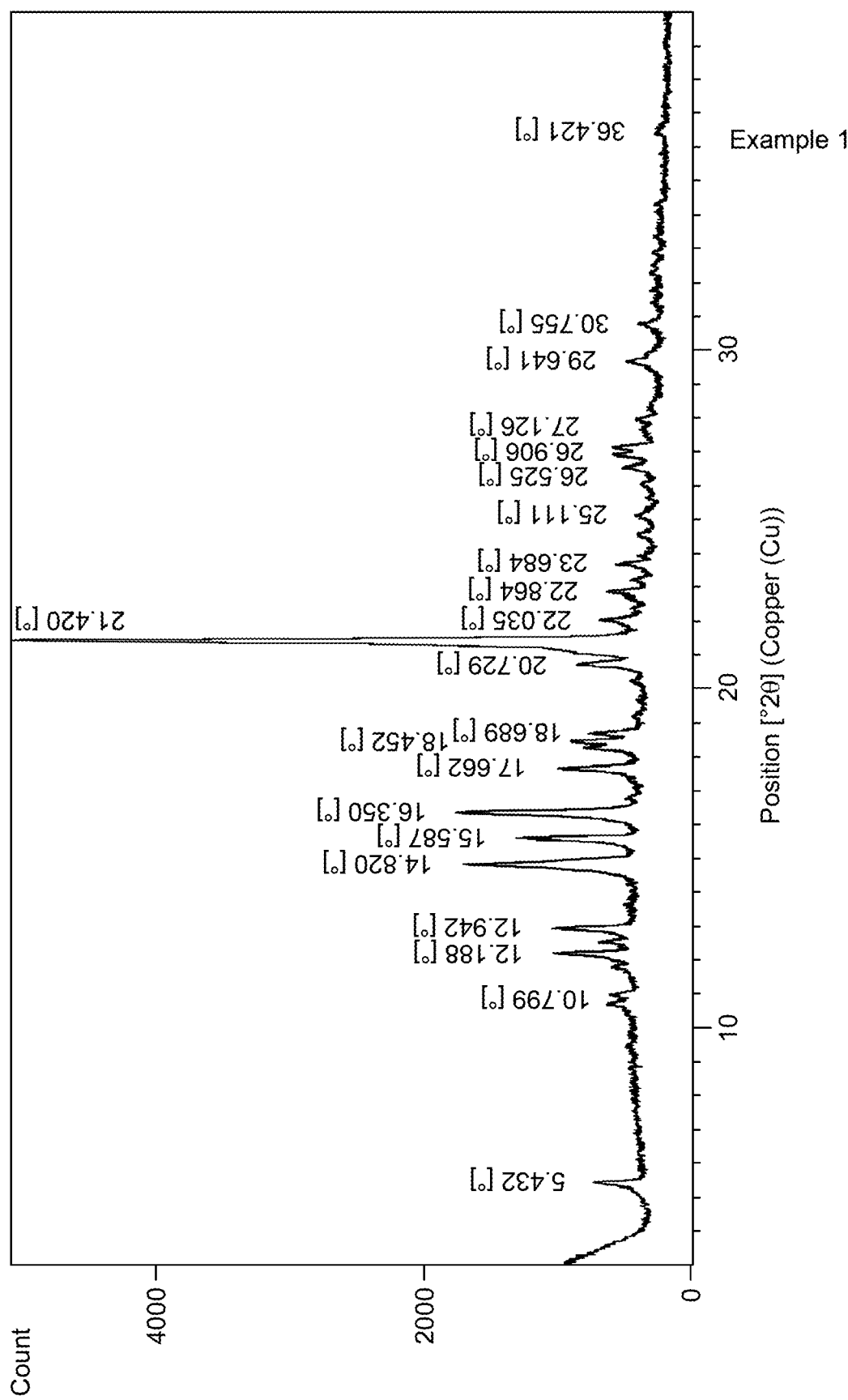
FIG. 1 is an X-ray powder diffraction pattern of the crystal form A of Zanubrutinib.
Figure 2:
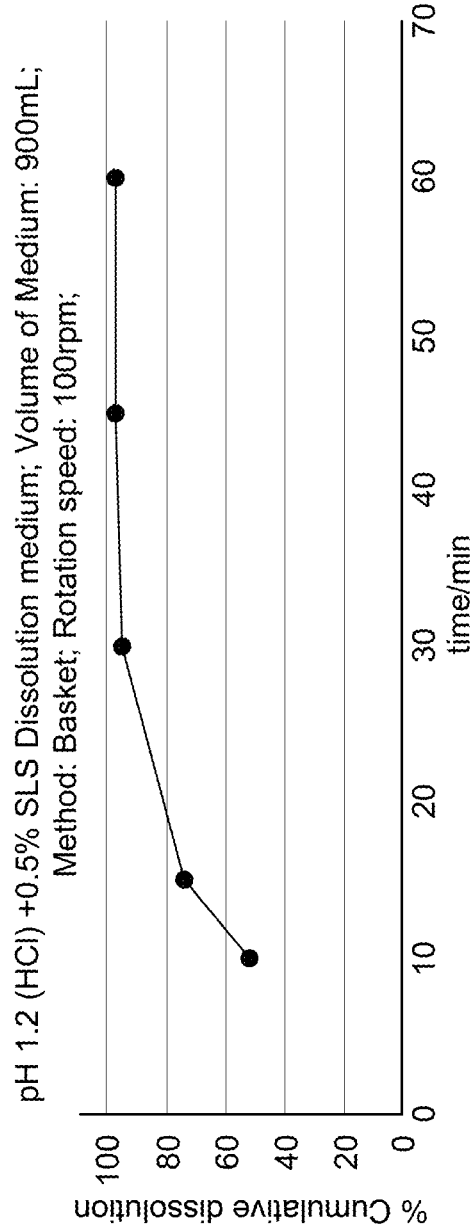
FIG. 2 is a schematic diagram of the cumulative drug dissolution (in vitro dissolution) of the solid tablet for oral administrations of Zanubrutinib in Example 1.

Drug Cumulative Dissolution (In Vitro Dissolution) Test: The in vitro dissolution experiment is determined by an automatic sampling dissolution tester (Model: 708+850DS, purchased from AGILENT), according to USP<711>, the "dissolution" is determined using the basket method, the automatic sampling dissolution tester is set at a water bath temperature of 37±0.5° C., at a rotating speed of 100 rpm, with a pH 1.2 (HCl)+0.5% SLS dissolution medium of a volume of 900 mL. Samples are taken at 10 min, 15 min, 30 min, 45 min, and 60 min, and all samples are passed through a 0.45 μm filter membrane, and the samples are determined and analyzed according to the sample dissolution test method. As shown in FIG. 2, when the Zanubrutinib solid tablet for oral administration of the present invention is in a pH 1.2 (HCl)+0.5% SLS medium, more than 90% of Zanubrutinib is dissolved at 30 minutes, which can meet the requirements of rapid release.

In the following Examples 2-12, the drug cumulative dissolution (in vitro dissolution) are all measured according to the method of Example 1.

Example 2

Preparation of Solid Tablet for Oral Administrations of Zanubrutinib, Specification: 160 mg
Prescription (Per 100 g Plain Tablets):

| | |
|---|---|
| Zanubrutinib (Crystal form A) | 36.2 g |
| Lactose | 55.6 g |
| Croscarmellose sodium | 2.2 g |
| Colloidal silica | 4.3 g |
| Sodium lauryl sulfate | 1.1 g |
| Magnesium stearate | 0.5 g |

Preparation Process: 55.6 g of lactose, 2.2 g of croscarmellose sodium, 1.1 g of sodium lauryl sulfate, 4.3 g of colloidal silica and 36.2 g of Zanubrutinib are added into a high-shear granulator and mixed for 5 minutes, an appropriate amount of purified water is added for granulation, followed by dying and then sizing, and 0.5 g of magnesium stearate is further added and mixed. After mixing, the above ingredients are pressed into tablets to obtain plain tablets, that is, an solid tablet for oral administration containing Zanubrutinib.

Drug Cumulative Dissolution (In Vitro Dissolution) Test: About 90% of Zanubrutinib is dissolved at 30 minutes.

Example 3

Preparation of Solid Tablet for Oral Administrations of Zanubrutinib, Specification: 160 mg Prescription (Per 100 g Plain Tablets):

| | |
|---|---|
| Zanubrutinib (Crystal form A) | 33.3 g |
| Lactose | 49.2 g |
| Hypromellose | 2 g |
| Croscarmellose sodium | 2 g |
| Colloidal silica | 4 g |
| Sodium lauryl sulfate | 1 g |
| Microcrystalline cellulose | 8 g |
| Magnesium stearate | 0.5 g |

Preparation Process: 49.2 g of lactose, 2 g of croscarmellose sodium, 1 g of sodium lauryl sulfate and 33.3 g of Zanubrutinib are added into a high-shear granulator and mixed for 5 minutes, 2 g of hypromellose aqueous solution is added for granulation, followed by dying and then sizing, 4 g of colloidal silica, 8 g of microcrystalline cellulose and 0.5 g of magnesium stearate are further added and mixed. After mixing, the above ingredients are pressed into tablets to obtain plain tablets, that is, an solid tablet for oral administration containing Zanubrutinib.

Example 4

Preparation of Solid Tablet for Oral Administrations of Zanubrutinib, Specification: 320 mg Prescription (Per 100 g Plain Tablets):

| | |
|---|---|
| Zanubrutinib (Crystal form A) | 50 g |
| Croscarmellose sodium | 4 g |
| Colloidal silica | 12.0 g |
| Sodium lauryl sulfate | 1 g |
| Microcrystalline cellulose | 32.5 g |
| Magnesium stearate | 0.5 g |
| Opadry | 1.5 g |

Preparation Process: 50 g of Zanubrutinib, 4 g of croscarmellose sodium, 12.0 g of colloidal silica, 1 g of sodium lauryl sulfate, 32.5 g of microcrystalline cellulose are sieved and then mixed in a high-shear granulator, then 0.5 g of magnesium stearate is added and mixed uniformly. The mixed powder is pressed directly to obtain plain tablets. The above-mentioned plain tablets are coated with a coating liquid containing 2.4 g of Opadry to obtain solid tablet for oral administrations containing Zanubrutinib.

Drug Cumulative Dissolution (In Vitro Dissolution) Test: The dissolution rate (%) of the drug at 30 minutes is about 80%.

Example 5

Preparation of Solid Tablet for Oral Administrations of Zanubrutinib, Specification: 80 mg Prescription (Per 100 g Plain Tablets):

| | |
|---|---|
| Zanubrutinib (Crystal form A) | 26.7 g |
| Lactose | 23.8 g |
| Croscarmellose sodium | 2 g |
| Colloidal silica | 4 g |
| Sodium lauryl sulfate | 1 g |
| Microcrystalline cellulose | 40 g |
| Hypromellose | 2 g |
| Magnesium stearate | 0.5 g |
| Opadry | 1.5 g |

Preparation Process: 23.8 g of lactose, 40 g of microcrystalline cellulose, 2 g of croscarmellose sodium, 1 g of sodium lauryl sulfate, 4 g of colloidal silica, and 26.7 g of Zanubrutinib are added to a fluidized bed, then 2 g of a hypromellose aqueous solution is sprayed for granulation, followed by drying and then magnesium stearate is added and mixed. After mixing, the above ingredients are pressed into tablets to obtain plain tablets. The above-mentioned plain tablets are coated with a coating liquid containing 1.5 g of Opadry to obtain solid tablet for oral administrations containing Zanubrutinib.

Example 6

Preparation of Solid Tablet for Oral Administrations of Zanubrutinib, Specification: 80 mg Prescription (Per 100 g Plain Tablets):

| | |
|---|---|
| Zanubrutinib (Crystal form A) | 26.7 g |
| Lactose | 35.8 g |
| Croscarmellose sodium | 2 g |
| Colloidal silica | 4 g |
| Sodium lauryl sulfate | 1 g |
| Silicified microcrystalline cellulose | 30 g |
| Magnesium stearate | 0.5 g |

Preparation Process: 26.7 g of Zanubrutinib, 2 g of croscarmellose sodium, 4 g of colloidal silica, 1 g of sodium lauryl sulfate, 35.8 g of lactose and 30 g of silicified microcrystalline cellulose are sieved and then mixed in a high-shear granulator, then 0.5 g of magnesium stearate is added and mixed uniformly. The powder is pressed into tablets directly, coated with an Opadry coating liquid to obtain solid tablet for oral administrations containing Zanubrutinib.

Example 7

Preparation of Solid Tablet for Oral Administrations of Zanubrutinib, Specification: 320 mg Prescription (Per 100 g Plain Tablets):

| | |
|---|---|
| Zanubrutinib (Crystal form A) | 50.0 g |
| Lactose | 36.5 g |
| Croscarmellose sodium | 4 g |
| Colloidal silica | 8 g |
| Sodium lauryl sulfate | 1 g |
| Magnesium stearate | 0.5 g |

Preparation Process: 50.0 g of Zanubrutinib, 4 g of croscarmellose sodium, 8 g of colloidal silica, 1 g of sodium lauryl sulfate, 36.5 g of lactose are sieved and then mixed in a high-shear granulator, then 0.5 g of magnesium stearate is added and mixed uniformly. The powder is pressed directly into tablets to obtain plain tablets, that is, an solid tablet for oral administration containing Zanubrutinib.

Drug Cumulative Dissolution (In Vitro Dissolution) Test: The dissolution rate (%) of the drug at 30 minutes is about 40%.

Example 8

Preparation of Solid Tablet for Oral Administrations of Zanubrutinib, Specification: 320 mg
Prescription (Per 100 g Plain Tablets):

| Zanubrutinib (Crystal form A) | 50.0 g |
| Croscarmellose sodium | 4 g |
| Colloidal silica | 8 g |
| Sodium lauryl sulfate | 1 g |
| Microcrystalline cellulose | 36.5 g |
| Magnesium stearate | 0.5 g |

Preparation Process: 50.0 g of Zanubrutinib, 36.5 g of microcrystalline cellulose, 4 g of croscarmellose sodium, 8 g of colloidal silica, 1 g of sodium lauryl sulfate are sieved and then mixed in a high-shear granulator, then 0.5 g of magnesium stearate is added and mixed uniformly. The powder is pressed directly into tablets to obtain plain tablets, that is, an solid tablet for oral administration containing Zanubrutinib.

Figure 3:
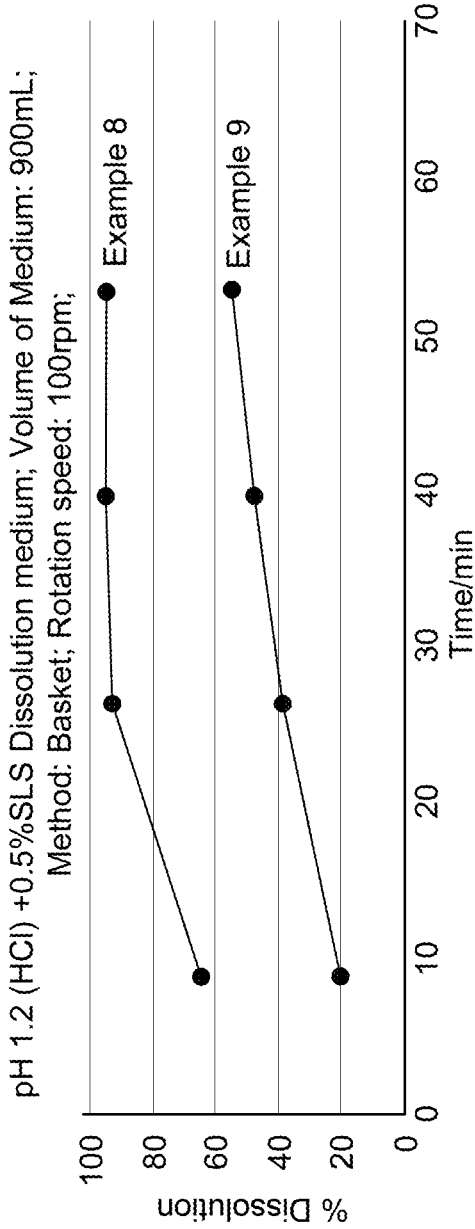
FIG. 3 is a schematic diagram of the cumulative drug dissolution (in vitro dissolution) of the solid tablet for oral administrations of Zanubrutinib in Example 8 and Example 9. It can be seen therefrom that the drug dissolution rate of Example 8 is significantly better than that of Example 9.

Drug Cumulative Dissolution (In Vitro Dissolution) Test: The dissolution curve of the drug is shown in FIG. 3. It can be seen that the dissolution is greater than 80% at 30 minutes.

Example 9

Preparation of Solid Tablet for Oral Administrations of Zanubrutinib, Specification: 320 mg
Prescription (Per 100 g Plain Tablets):

| Zanubrutinib (Crystal form A) | 60.0 g |
| Croscarmellose sodium | 4 g |
| Colloidal silica | 0.8 g |
| Sodium lauryl sulfate | 1 g |
| Microcrystalline cellulose | 33.7 g |
| Magnesium stearate | 0.5 g |

Preparation Process: 60 g of Zanubrutinib, 33.7 g of microcrystalline cellulose, 4 g of croscarmellose sodium, 0.8 g of colloidal silica, 1 g of sodium lauryl sulfate are sieved and then mixed in a high-shear granulator, then 0.5 g of magnesium stearate is added and mixed uniformly. The powder is pressed directly into tablets to obtain plain tablets, that is, an solid tablet for oral administration containing Zanubrutinib.

Drug Cumulative Dissolution (In Vitro Dissolution) Test: The dissolution curve of the drug is shown in FIG. 3. It can be seen that the dissolution is less than 60% at 30 minutes.

Example 10

Preparation of Solid Tablet for Oral Administrations of Zanubrutinib, Specification: 320 mg
Prescription (Per 100 g Plain Tablets):

| Zanubrutinib (Crystal form A) | 46.69 g |
| Croscarmellose sodium | 4.38 g |
| Colloidal silica | 0.88 g |
| Sodium lauryl sulfate | 0.88 g |
| Microcrystalline cellulose | 46.69 g |
| Magnesium stearate | 0.50 g |

Preparation Process: 53.2 g of lactose, 2 g of croscarmellose sodium, 1 g of sodium lauryl sulfate and 34.8 g of Zanubrutinib are added into a high-shear granulator (MYCROMIX, manufactured by BOSCH) and mixed for 5 minutes, an appropriate amount of purified water is added for granulation, followed by dying and then sizing, 4.5 g of colloidal silica, 4 g of microcrystalline cellulose and 0.5 g of magnesium stearate are further added and mixed. After mixing, the above ingredients are pressed into tablets to obtain plain tablets, that is, an solid tablet for oral administration containing Zanubrutinib.

Drug Cumulative Dissolution (In Vitro Dissolution) Test: The dissolution rate (%) of the drug at 60 minutes is about 80%.

Example 11

Preparation of Solid Tablet for Oral Administrations of Zanubrutinib, Specification: 320 mg
Prescription (Per 100 g Plain Tablets):

| Zanubrutinib (Crystal form A) | 46.69 g |
| Lactose | 46.69 g |
| Croscarmellose sodium | 4.38 g |
| Colloidal silica | 0.88 g |
| Sodium lauryl sulfate | 0.88 g |
| Magnesium stearate | 0.50 g |

Preparation Process: According to a method similar to Example 10, the solid tablet for oral administrations containing Zanubrutinib can be prepared.

Drug Cumulative Dissolution (In Vitro Dissolution) Test: The dissolution rate (%) of the drug at 60 minutes is less than 80%.

Example 12

Preparation of Solid Tablet for Oral Administrations of Zanubrutinib, Specification: 320 mg
Prescription (Per 100 g Plain Tablets):

| Zanubrutinib (Crystal form A) | 22.21 g |
| Croscarmellose sodium | 3.00 g |
| Colloidal silica | 0.50 g |
| Sodium lauryl sulfate | 0.50 g |
| Microcrystalline cellulose | 73.29 g |
| Magnesium stearate | 0.50 g |

Preparation Process: According to a method similar to Example 10, the solid tablet for oral administrations containing Zanubrutinib can be prepared.

Although the foregoing description teaches the principles of the present invention and provides examples for the purpose of illustration, the practice of the present invention includes all common changes, adaptations and/or modifications within the scope of the following claims. The references involved in this disclosure are incorporated herein by reference.

What is claimed is:

1. A solid tablet for oral administration comprising:
   80 mg, 160 mg, or 320 mg micronized zanubrutinib in crystal form A;
   a filler comprising lactose in an amount of about 20% to about 70% by mass of the solid tablet; and
   a glidant in an amount from about 0.1% to about 20% by mass of the solid tablet, wherein the glidant is powdered cellulose, magnesium trisilicate, colloidal silica, talc powder, or any combination thereof,
   provided that if the solid tablet contains lactose as the only filler in the solid tablet, the amount of lactose in the solid tablet is not less than that of zanubrutinib,
   wherein at least about 80% of zanubrutinib is dissolved within 60 minutes in a solution having a pH value of about 1.2 and comprising sodium lauryl sulfate in an amount of about 0.5% by mass of the solution at a temperature of 37±0.5° C. with a rotating speed of 100 rpm.

2. The solid tablet of claim 1, further comprising a binder, a disintegrant, a wetting agent, a lubricant, or any combination thereof.

3. The solid tablet of claim 1, wherein the filler further comprises starch, sucrose, microcrystalline cellulose, mannitol, pregelatinized starch, glucose, maltodextrin, cyclodextrin, cellulose, silicified microcrystalline cellulose, or any combination thereof.

4. The solid tablet of claim 1, further comprising microcrystalline cellulose in an amount of about 10% to about 50% by mass of the solid tablet.

5. The solid tablet of claim 1, further comprising microcrystalline cellulose in an amount of less than about 50% by mass of the solid tablet.

6. The solid tablet of claim 2, wherein the binder is starch, hypromellose, polyvinylpyrrolidone, sodium carboxymethyl cellulose, hydroxypropyl cellulose, methyl cellulose, ethyl cellulose, gelatin, sucrose, or any combination thereof.

7. The solid tablet of claim 1, further comprising polyvinylpyrrolidone in an amount of less than about 10% by mass of the solid tablet.

8. The solid tablet of claim 2, wherein the disintegrant is sodium carboxymethyl starch, low-substituted hydroxypropyl cellulose, crospovidone, croscarmellose sodium, croscarmellose, methyl cellulose, pregelatinized starch, sodium alginate, or any combination thereof.

9. The solid tablet of claim 1, further comprising croscarmellose sodium in an amount of about 0.5% to about 5% by mass of the solid tablet.

10. The solid tablet of claim 1, further comprising sodium lauryl sulfate in an amount of about 0.5% to about 5% by mass of the solid tablet.

11. The solid tablet of claim 1, wherein the glidant is colloidal silica.

12. The solid tablet of claim 2, wherein the lubricant is zinc stearate, glyceryl monostearate, glyceryl palmitate stearate, magnesium stearate, sodium fumarate stearate, or any combination thereof.

13. The solid tablet of claim 1, further comprising magnesium stearate in an amount of about 0.1% to about 2% by mass of the solid tablet.

14. The solid tablet of claim 1, further comprising a film coating powder, polyvinyl alcohol, hydroxypropyl cellulose, polyethylene glycol, or any combination thereof.

15. The solid tablet of claim 1, comprising:
    80 mg, 160 mg, or 320 mg micronized zanubrutinib in crystal form A;
    colloidal silica in an amount of about 0.88% to about 12% by mass of the solid tablet;
    lactose in an amount of about 40% to about 60% by mass of the solid tablet;
    microcrystalline cellulose in an amount of about 4% to about 10% by mass of the solid tablet;
    polyvinylpyrrolidone in an amount of less than about 5% by mass of the solid tablet;
    croscarmellose sodium in an amount of about 0.5% to about 5% by mass of the solid tablet;
    sodium lauryl sulfate in an amount of about 0.5% to about 1.0% by mass of the solid tablet; and
    magnesium stearate in an amount of about 0.3% to about 1% by mass of the solid tablet.

16. The solid tablet of claim 1, comprising:
    80 mg, 160 mg, or 320 mg micronized zanubrutinib in crystal form A;
    colloidal silica in an amount of about 0.88% to about 12% by mass of the solid tablet;
    lactose in an amount of about 40% to about 60% by mass of the solid tablet;
    polyvinylpyrrolidone in an amount of less than about 5% by mass of the solid tablet;
    croscarmellose sodium in an amount of about 0.5% to about 5% by mass of the solid tablet;
    sodium lauryl sulfate in an amount of about 0.5% to about 1.0% by mass of the solid tablet; and
    magnesium stearate in an amount of about 0.3% to about 1% by mass of the solid tablet.

17. A solid tablet, comprising:
    80 mg, 160 mg, or 320 mg micronized zanubrutinib in crystal form A;
    colloidal silica in an amount of about 0.88% to about 12% by mass of the solid tablet;
    microcrystalline cellulose in an amount of about 30% to about 50% by mass of the solid tablet;
    polyvinylpyrrolidone in an amount less than about 5% by mass of the solid tablet;
    croscarmellose sodium in an amount of about 0.5% to about 5% by mass of the solid tablet;
    sodium lauryl sulfate in an amount of about 0.5% to about 1.0% by mass of the solid tablet; and
    magnesium in an amount of about 0.3% to about 1% by mass of the solid tablet, wherein at least about 80% of zanubrutinib is dissolved within 60 minutes in a solution having a pH value of about 1.2 and comprising sodium lauryl sulfate in an amount of about 0.5% by mass of the solution at a temperature of 37±0.5° C. with a rotating speed of 100 rpm.

18. The solid tablet of claim 1, wherein the micronized zanubrutinib has a particle size of no more than 40 µm.

19. The solid tablet of claim 1 comprising 160 mg zanubrutinib.

20. The solid tablet of claim 1 comprising 80 mg zanubrutinib.

21. The solid tablet of claim 1 comprising 320 mg zanubrutinib.

22. The solid tablet of claim 19, comprising lactose in an amount of about 52% by mass of the solid tablet;
    microcrystalline cellulose in an amount of about 10% by mass of the solid tablet;

polyvinylpyrrolidone in an amount of about 3% by mass of the solid tablet;
croscarmellose sodium in an amount of about 5% by mass of the solid tablet;
sodium lauryl sulfate in an amount of about 0.5% by mass of the solid tablet;
colloidal silica in an amount of about 2% by mass of the solid tablet; and
magnesium stearate in an amount of about 0.8% by mass of the solid tablet.

23. The solid tablet of claim 22, wherein
more than about 90% of zanubrutinib is dissolved within about 30 minutes in a solution having a pH value of about 1.2 and comprising sodium lauryl sulfate in an amount of about 0.5% by mass of the solution at a temperature of 37±0.5° C. with a rotating speed of 100 rpm.

* * * * *